| (12) | United States Patent | (10) Patent No.: | US 6,173,714 B1 |
|---|---|---|---|
| | Cho | (45) Date of Patent: | *Jan. 16, 2001 |

(54) METHOD FOR SURGICALLY ENLARGING A PENIS

(76) Inventor: Kang-Seon Cho, Samseong-dong, Kangnam-gu, Seoul (KR)

( * ) Notice: Under 35 U.S.C. 154(b), the term of this patent shall be extended for 0 days.

This patent is subject to a terminal disclaimer.

(21) Appl. No.: 09/296,971

(22) Filed: Apr. 22, 1999

Related U.S. Application Data

(63) Continuation of application No. 09/111,643, filed on Jul. 8, 1998, now Pat. No. 5,921,246.

(30) Foreign Application Priority Data

Jan. 19, 1998 (KR) .................................................. 98-1452

(51) Int. Cl.[7] .................................................. A61B 19/00
(52) U.S. Cl. .............................................................. 128/898
(58) Field of Search .............................. 128/898; 623/11, 623/12, 66, 7; 600/36, 40

(56) References Cited

U.S. PATENT DOCUMENTS 5,921,246 * 7/1999 Cho ....................................... 128/898

FOREIGN PATENT DOCUMENTS

408257045 * 10/1996 (JP) .

* cited by examiner

Primary Examiner—David J. Isabella
Assistant Examiner—Kelly O'Hara
(74) Attorney, Agent, or Firm—Merchant & Gould P.C.

(57) ABSTRACT

A surgically enlarging method of microcaulia by which length and circumference of micropenis are simultaneously enlarged and expanded without incurring any deformation or side effect thereto, enabling the microcaulia patients to overcome the physical defect, shame and inferiority complex and thereby providing them with increased sexual self confidence.

5 Claims, 4 Drawing Sheets

METHOD FOR SURGICALLY ENLARGING A PENIS

This application is a Continuation of application Ser. No. 09/111,643, filed Jul. 8, 1998, which application(s) are incorporated herein by reference, U.S. Pat. No. 5,921,246.

BACKGROUND OF THE INVENTION

1. Field of the Invention

The present invention relates to a surgically enlarging method of microcaulia adapted to enlarge or elongate length and circumference of a penis in an unerectile state, without giving rise to deformation or side effect thereto alleviating shame of microcaulia neurosis, eliminating an inferiority complex, and thereby providing emotional stability for maintenance of a normal life.

2. Description of the Prior Art

Generally, microcaulia neurosis denotes a variety of neurotic those of other men.

There are cases of underdeveloped micropenis, however where the self-consciousness associated with believing the male organ is smaller dominates even though the penis has developed objectively, normally.

There is no standardized definition of microcaulia, however, a penis is regarded as small when it is measured less than 4 cm from an upper pubis to a tip end thereof in the absence of erection state or when the standard deviation is more than 2 compared with a normal penile length of the same age group.

The microcaulia occurs when the penis is underdeveloped due to deficiencies of testosterone. This should not be treated as an independent physical disorder but regarded as a general disorder affecting the whole target tissue against androgen.

In this case, testicles are generally small or the micropenis is accompanied by retained testicles. At times, underdeveloped scrotum happens, and chances are that patients of micropenis suffer from prostate problems and incomplete physical growth at post-pubescence.

Microcaulia neurotics (patients) usually have inferiority complexes and lack self-confidence in everyday lives, and they especially especially hate to go out nude to people-gathering places such as public bath houses and the like, thereby experiencing inconveniences in their social lives.

As mentioned above, in order to treat the microcaulia neurotics, it is necessary to both enlarge and expand the length and girth of a penis and at the same time to maintain a natural look thereof.

Currently, surgical treatment include a girth enlargement surgery of penis by way of derma fat transplant, a length elongation surgery of penis by way of ligament cut and expansion of skin length and the like. These kinds of surgeries are done separately.

In more detail, the former method of girth enlargement surgery is performed by tearing off derma fat from a part of the body, incising the skin of the penis at a predetermined width and grafting the torn derma fat to the girth of the penis, except for urethra area, to thereby expand the circumference of the penis.

The latter method of length elongation surgery is carried out by incising a suspensor ligament of the penis, expanding the skin length and enlarging the overall length of penis, whereby, in case of success in surgery, the penis is in most cases enlarged lengthwise by as much as 2.5 cm in an unerectile state to the approval of the patient.

SUMMARY OF THE INVENTION

However, there is a problem in the girth enlargement surgery in that only the girth is expanded and extra surgery should be performed to get an effective treatment of length elongation. There is also a problem in the length elongation surgery in that the success rate is low, and even in case of success, the elongated length is not that long (generally less than 2.5 cm) and the odds after the surgery are that length of the penis is rather shortened during erection or that the penis trends to droop down.

There is still another problem in the length elongation surgery in that the shape of penis is unnaturally deformed, thereby providing a cause of another complex feeling in that these kinds of surgical methods cannot be regarded as appropriate cures to the microcaulia neurotics.

Accordingly, the present invention is presented to solve the afore-mentioned problems and it is an object of the present invention to provide a surgically enlarging method of microcaulia adapted to simultaneously enlarge and lengthen the girth and the length of a micropenis with no side effect incurred and with an increased surgical success rate (99.8%) and at the same time to maintain a natural look thereof.

In accordance with the objects of the present invention there is provided a surgically enlarging method of microcaulia, the method comprising the steps of:

removing a piece of dermal fat tissue from a body of a patient;

incising a skin of the penis and dissecting a subcutaneous tissue to expose an area and grafting the removed dermal fat tissue onto the exposed are of penis in a state of the penis being pulled to a front area thereof; and covering the grafted dermal fat tissue with the dissected subcutaneous tissue and the skin of penis and suturing.

BRIEF DESCRIPTION OF THE DRAWINGS

For fuller understanding of the nature and objects of the invention, reference should be made to the following detailed description taken in conjunction with the accompanying drawings in which.

DETAILED DESCRIPTION OF THE INVENTION

A preferred embodiment of the present invention will now be described in detail with reference to the accompanying drawings.

Figure 1:
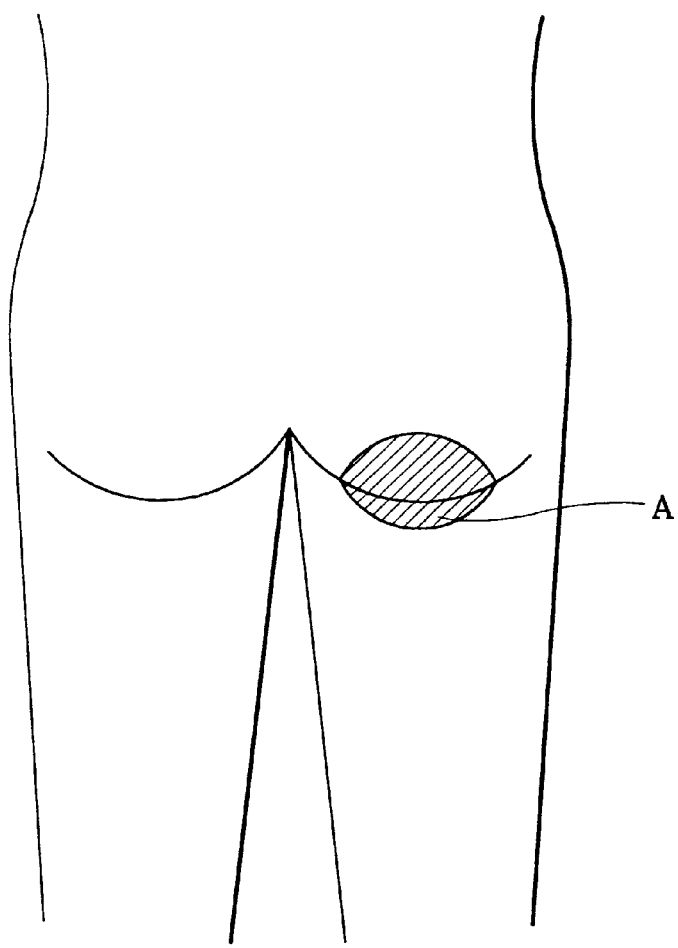
FIG. 1 is a schematic diagram for illustrating a removed of derma fat from a wrinkled hip area of a patient.

First of all, the microcaulia neurotic is layed down on his belly to remove as much derma fat (A) as possible from part of the body, preferably from a wrinkled hip area as illustrated in FIG. 1, the derma fat (A) being large enough to cover the penis circumferentially.

The derma fat is placed in cold storage at a low temperature, preferably 0° C., right after it is taken out. The vulnus (torn) area where the derma fat is taken out is sutured by cosmetic surgery.

At this time, the removed derma fat should be long enough and wide enough to circumfuse an erect penis lest there should be any problem in suturing the vulnus area. The reason for putting the removed derma fat (A) in cold storage is to minimize damage to the cells in the derma fat (A) before the graft is performed (approximately 60 minutes).

The patient is then laid on his back after the suture and cosmetic surgery are carried out, and the patient's penis is cut by a surgical scalpel (See FIG. 3) and the skin of the penis is fully ablated from a cut line (B) in the direction of glans and the upper part of the pubis ("C" direction) to expose the Buck's Fascia (Buck's muscle membrane). (See FIG. 4)

Figure 4:
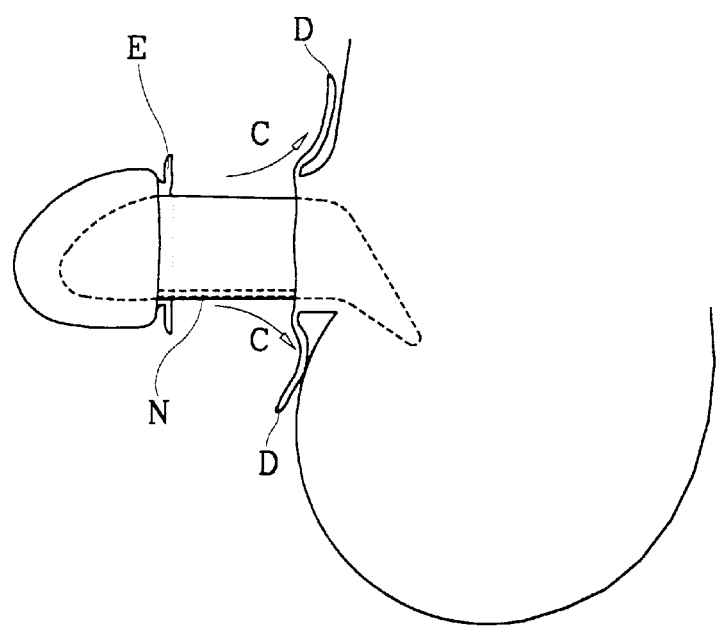
FIG. 4 is a schematic diagram for illustrating ablations of skin of the penis from respective incision lines.

Reference symbol "D" in FIG. 4 is the skin of the penis ablated from the upper part of the pubis ("C" direction) and "E" is another skin of penis separated from the glans.

Figure 5:
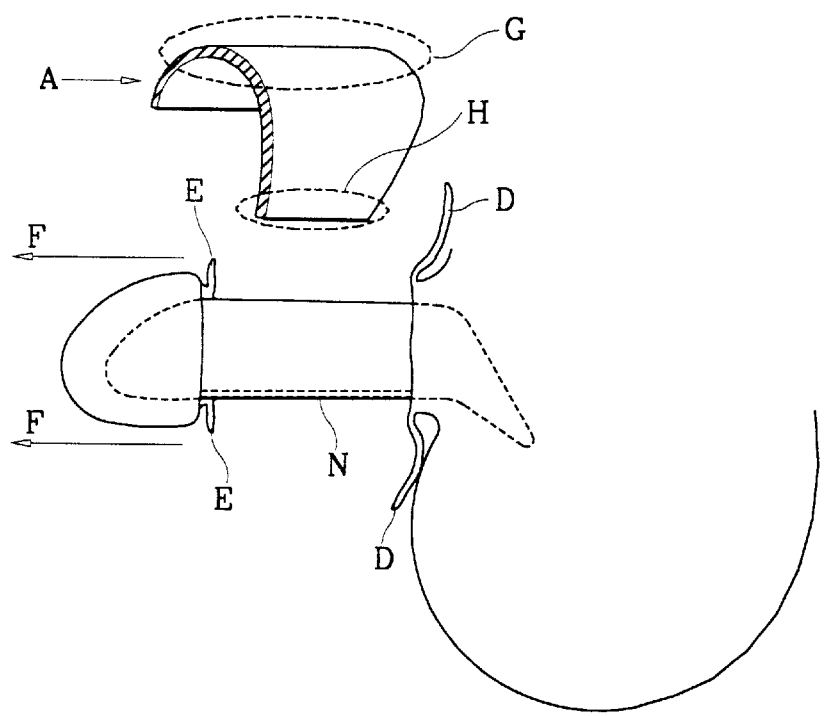
FIG. 5 is a schematic diagram for illustrating an implantation of derma fat removed from the ablated penis area in a state of the penis maximally pulled to the front thereof.

Next, as illustrated in FIG. 5, the penis of the patient is maximally pulled forward ("F" direction) to almost the same length of erection under which state the cold-stored derma fat (A) is grafted to the ablated area of the penis.

Figure 2:
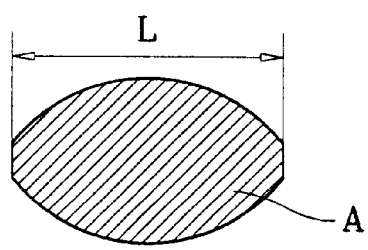
FIG. 2 is a schematic diagram for illustrating a derma fat cut at both sides, leaving the length (L) of the derma fat to fully cover the circumference of a penis.

At this time, the removed derma fat (A) is cut at both end sides except for the portion which can fully encompass the penis, as illustrated in FIG. 2.

Successively, the derma layer is made to face outside of the penis in an unfolded state, that is, in a non-stretched state of the dermal fat (A) and the fat layer is made to face the penis. The widest area (G) of the derma fat (A) is positioned at an upper or dorsal side (12 o'clock direction) of the penis and the narrowest area (H) is made to be situated at a ventral location under the penis (6 o'clock direction).

At this location, the derma fat (A) is made to be positioned in such a way as to encompass the whole length of the penis including the urethra part (N) such that the derma fat (A) should have enough room not to interfere with circumferential expansion of the penis when it is erected. The derma fat (A) is then sutured and fixed to Buck's Fascia.

Figure 6:
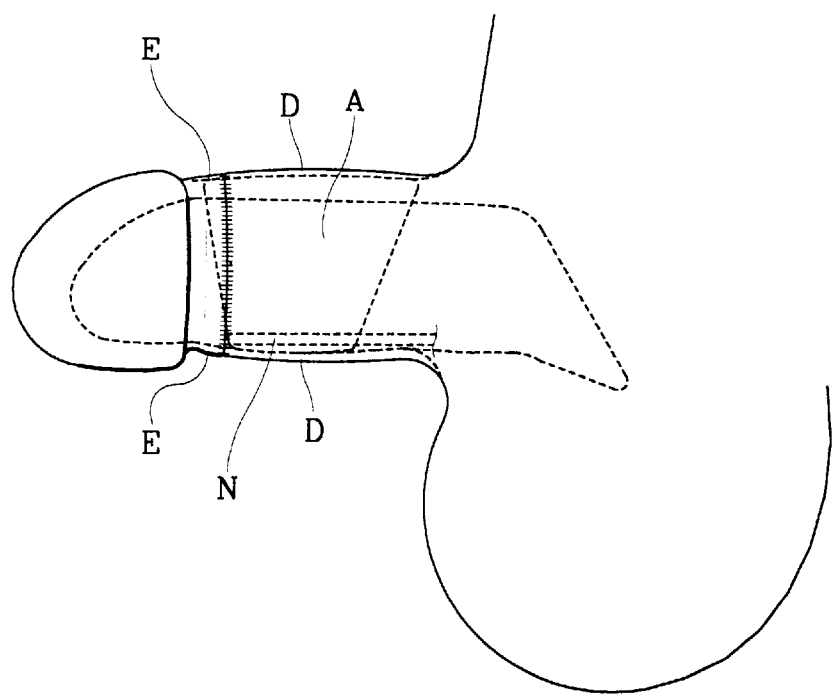
FIG. 6 is a schematic diagram for illustrating a sutured state of the ablated skin of penis onto the derma fat after the derma fat is implanted.

The derma fat (A) grafted to the penis is sequentially covered with and sutured by subcutaneous tissue and skin tissue of the penis respectively ablated towards the glans and the upper part of pubis ("C" direction), as illustrated in FIG. 6.

Figure 7:
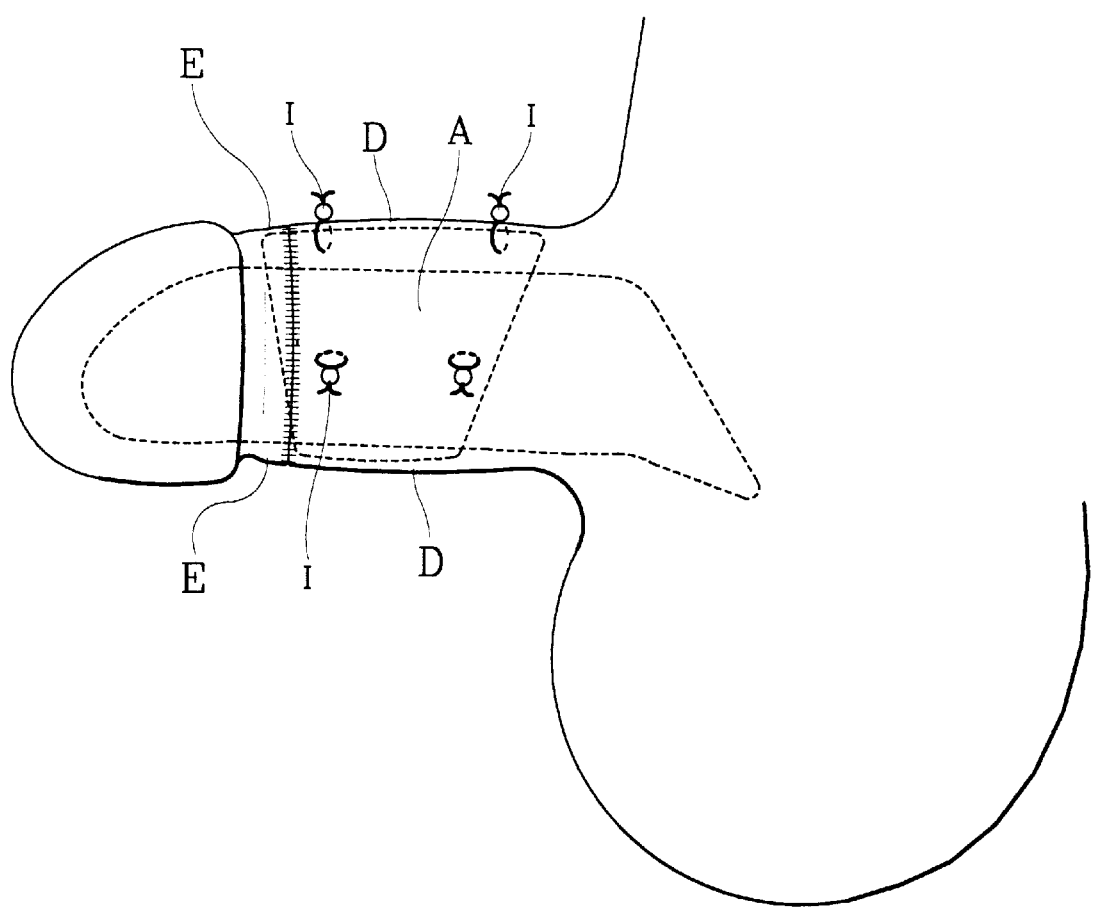
FIG. 7 is a schematic diagram for illustrating a sutured state where an original skin tissue and a grafted derma fat tissue are all sewn at an external side of the penis in order to mutually fix the original skin tissue and the derma fat tissue grafted on the penis and petrolatum gauze is applied to the external side of the penis skin on which a knot is tied for suture.

At the next stage, as illustrated in FIG. 7, the original skin. tissue and the grafted derma fat tissue are all sewn together at an external side of the penis so as to be fixed therebetween. A petrolatum gauze (I) on which a knot is made and sutured is then applied to the external side of the penis.

Figure 3:
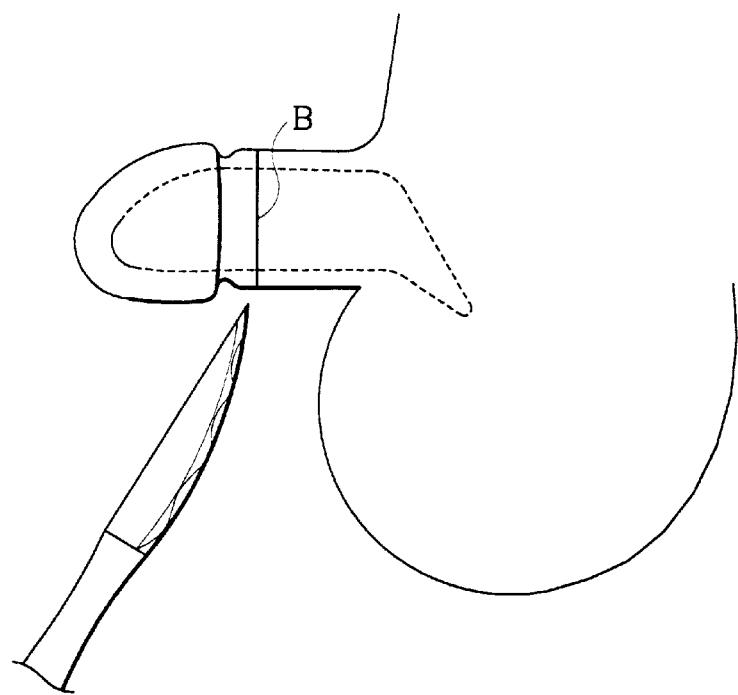
FIG. 3 is a schematic diagram for illustrating an incision of a penis.

Accordingly, as comparatively seen in FIG. 3 and FIG. 6, the hip derma fat tissue (A) implanted to the penis is much duller, slower and more insensitive in shrinkage rate than the cancellous tissue of the penis such that the length of the penis pulled towards the front end thereof ("F" direction) markedly prevents the shrinkage of the penis when the two tissues are sewn together.

After the surgery, the normal length of the penis is consequently maintained with the addition of grafted derma fat (A) in width (G) and the length of the glans, so that circumference of the penis is enlarged as much as the thickness of the derma fat (A) grafted to the skin of (D) the penis.

Furthermore, the derma fat (A) implanted to the penis has the same tissue as the cell tissue of the penis such that the fat (A) is easily assimilated into the tissue of the penis without any side effect.

As many as 150 microcaulia patients who had undergone the surgery according to the present invention have been randomly chosen in a survey to obtain data in the length and girth of the penis before and after the operation, which is shown in table 1.

TABLE 1

| Time | Patients checked | length (average) | girth (average) |
| --- | --- | --- | --- |
| before surgery | 105 | 4.5 Cm | 7.1 Cm |
| 2–3 months after surgery | 82 | 8.3 Cm | 12.1 Cm |
| 4–12 months after surgery | 23 | 8.1 Cm | 11.3 Cm |
| 13–60 months (average 31 months) after surgery | 18 | 8.0 Cm | 10.7 Cm |

Furthermore, the degree of satisfaction after the surgery according to the present invention is given in Table 2.

TABLE 2

| 105 Patients checked | greatly improved | a little improved |
| --- | --- | --- |
| Public bath evasive syndrome | 74 (70.5%) | 10 |
| inferiority complex | 77 (73.3%) | 18 |
| sexual self-confidence | 36 (34.3%) | 22 |

Still furthermore, sexual life affected after the surgery according to the present invention is presented in Table 3.

TABLE 3

| 93 patients checked | Improved |
| --- | --- |
| ejaculation time | 56 (60.2%) |
| partner's satisfaction | 45 (48.4%) |
| patient's satisfaction | 58 (62.4%) |
| erection power | 14 (15.1%) |

As apparent from the foregoing, there is an advantage in the surgically enlarging method of microcaulia in that the length and the circumference of micropenis are simultaneously enlarged and expanded without incurring any deformation or side effect thereto, thereby enabling the microcaulia neurotics to overcome the physical defect, shame and inferiority complex and providing them with increased sexual self confidence.

What is claimed is:

1. A method for surgically enlarging a penis, the method comprising the steps of:

removing a piece of dermal fat tissue from a body of a patient;

incising a skin of the penis and dissecting a subcutaneous tissue to expose an area and grafting the removed dermal fat tissue onto the exposed area of penis in a state of the penis being pulled to a front area thereof; and covering the grafted dermal fat tissue with the dissected subcutaneous tissue and the skin of penis and suturing.

2. The method as defined in claim 1, wherein the removed dermal fat tissue is grafted onto the exposed area of penis in a state of the penis being pulled to a front area thereof to the extent of erection state.

3. The method as defined in claim 1, wherein the removed dermal fat tissue is stored in low temperature state.

4. The method as defined in claim 1, wherein a dermal layer of the dermal fat tissue is made to face outside of the penis and a fat layer is made to face the penis where the widest area of the removed dermal fat tissue is positioned at a dorsal part of the penis and the narrowest area is made to be situated at a ventral part of the penis in an unfolded state.

5. The method as defined in claim 1, wherein the penis is exposed to a urethra part when the skin of the penis is incised and the subcutaneous tissue is dissected, and the dermal fat is grafted onto the dissected area of penis in a state of encompassing the whole circumference of the penis including the urethra part with enough room not to interfere with circumferential expansion of the penis when it is erected.

* * * * *

UNITED STATES PATENT AND TRADEMARK OFFICE
CERTIFICATE OF CORRECTION

PATENT NO. : 6,173,714 B1  Page 1 of 2
DATED : January 16, 2001
INVENTOR(S) : Cho It is certified that error appears in the above-identified patent and that said Letters Patent is hereby corrected as shown below:

<u>Title page,</u>
ABSTRACT, lines 6-7, "self confidence" should read -- self-confidence --

<u>Column 1,</u>
Lines 18-19, "those of other men." should read -- symptoms resulting from a feeling that one's penis is smaller than those of other men. --
Line 43, "especially especially" should read -- especially --
Line 50, "treatment" should read -- treatments --

<u>Column 2,</u>
Line 10, "trends" should read -- tends --
Line 12, insert -- the -- before "penis"
Line 17, "afore-mentioned" should read -- aforementioned --
Line 30, "exposed are" should read -- exposed area --
Line 40, "removed" should read -- removal --

<u>Column 3,</u>
Line 1, "layed" should read -- laid --
Line 17, "surgery are" should read -- surgery is --
Line 36, "dermal" should read -- derma --
Line 53, "skin." should read -- skin --

UNITED STATES PATENT AND TRADEMARK OFFICE
CERTIFICATE OF CORRECTION

PATENT NO. : 6,173,714 B1
DATED : January 16, 2001
INVENTOR(S) : Cho

It is certified that error appears in the above-identified patent and that said Letters Patent is hereby corrected as shown below:

<u>Column 4,</u>
Line 42, In Table 3, the first column, "ejeculation" should read -- ejaculation --

Signed and Sealed this

Fifth Day of March, 2002

Attest:

JAMES E. ROGAN
*Attesting Officer*   *Director of the United States Patent and Trademark Office*